US012733885B2

(12) United States Patent

Fujiwara et al.

(10) Patent No.: US 12,733,885 B2

(45) Date of Patent: Sep. 15, 2026

(54) POSTURE CONTROL DEVICE

(71) Applicants: TOYODA GOSEI CO., LTD., Kiyosu (JP); NATIONAL UNIVERSITY CORPORATION TOKAI NATIONAL HIGHER EDUCATION AND RESEARCH SYSTEM, Nagoya (JP)

(72) Inventors: Takeshi Fujiwara, Kiyosu (JP); Koichiro Tsuzuku, Kiyosu (JP); Hitoshi Hirata, Nagoya (JP); Shintaro Oyama, Nagoya (JP)

(73) Assignees: Toyoda Gosei Co., Ltd., Kiyosu (JP); National University Corporation Tokai National Higher Education and Research System, Nagoya (JP)

( * ) Notice: Subject to any disclaimer, the term of this patent is extended or adjusted under 35 U.S.C. 154(b) by 0 days.

(21) Appl. No.: 18/840,439

(22) PCT Filed: Mar. 24, 2022

(86) PCT No.: PCT/JP2022/014074

§ 371 (c)(1),
(2) Date: Aug. 21, 2024

(87) PCT Pub. No.: WO2023/181288

PCT Pub. Date: Sep. 28, 2023

(65) Prior Publication Data

US 2025/0152109 A1 May 15, 2025

(51) Int. Cl.

*G08B 23/00* (2006.01)
*A61B 5/00* (2006.01)
*A61B 5/103* (2006.01)

(52) U.S. Cl.

CPC ............ *A61B 5/746* (2013.01); *A61B 5/1038* (2013.01); *A61B 5/7405* (2013.01); *A61B 5/7455* (2013.01)

(58) Field of Classification Search

CPC ..... A61B 5/746; A61B 5/1038; A61B 5/7405; A61B 5/7455; A61B 5/1116; A61B 5/112;

(Continued)

(56) References Cited

U.S. PATENT DOCUMENTS 7,997,007 B2 * 8/2011 Sanabria-Hernandez .................. A43B 3/50 36/137
8,692,675 B2 * 4/2014 Agrawal ............. A61B 5/0051 600/587

(Continued)

FOREIGN PATENT DOCUMENTS

JP 2011-062298 A 3/2011
JP 4690890 B2 6/2011

(Continued)

OTHER PUBLICATIONS

International Search Report (ISR) (PCT Form PCT/ISA/210), in PCT/JP2022/014074, dated Jun. 14, 2022 (English Version).

*Primary Examiner* — Toan N Pham

(74) *Attorney, Agent, or Firm* — McGinn IP Law Group, PLLC

(57) ABSTRACT

A posture control device includes a posture information detection unit, a tactile stimulus application unit configured to apply tactile stimuli to the somatosensory receptors of a user, and an external tactile stimulus application unit configured to apply external tactile stimuli to the user. The posture information detection unit is configured to detect (Continued)

contact pressures at multiple parts of the sole and detect a change in posture based on temporal changes in the detected contact pressures. The external tactile stimulus application unit is configured to apply external tactile stimuli to the user, at a specified point in time that is based on a detection result of the posture information detection unit, to assist user posture control by integrating external tactile stimuli with tactile stimuli applied by the tactile stimulus application unit through sensory integration.

20 Claims, 3 Drawing Sheets

(58) Field of Classification Search
CPC ........ A61B 5/486; A61B 5/6807; A61H 1/02; A61H 3/00

See application file for complete search history.

(56) References Cited

U.S. PATENT DOCUMENTS

| | | | | |
|---|---|---|---|---|
| 8,968,218 | B2 * | 3/2015 | Wukasch ............ | A61B 5/6829 600/595 |
| 9,591,993 | B2 * | 3/2017 | Morris Bamberg . | A61B 5/0002 |
| 2007/0073196 | A1 | 3/2007 | Tanaka et al. | |
| 2010/0152619 | A1 * | 6/2010 | Kalpaxis .............. | A63F 13/211 600/592 |
| 2014/0266570 | A1 * | 9/2014 | Sharma ................... | A43B 3/48 340/4.12 |
| 2016/0143562 | A1 * | 5/2016 | Ashby ................... | A61B 5/486 600/595 |
| 2021/0186331 | A1 | 6/2021 | Roh et al. | |
| 2021/0259579 | A1 * | 8/2021 | Grant-Beuttler ..... | A61B 5/1038 |

FOREIGN PATENT DOCUMENTS

| | | | |
|---|---|---|---|
| JP | 2021-102043 | A | 7/2021 |
| JP | 2021-126172 | A | 9/2021 |
| WO | WO 2004/103244 | A1 | 12/2004 |

* cited by examiner

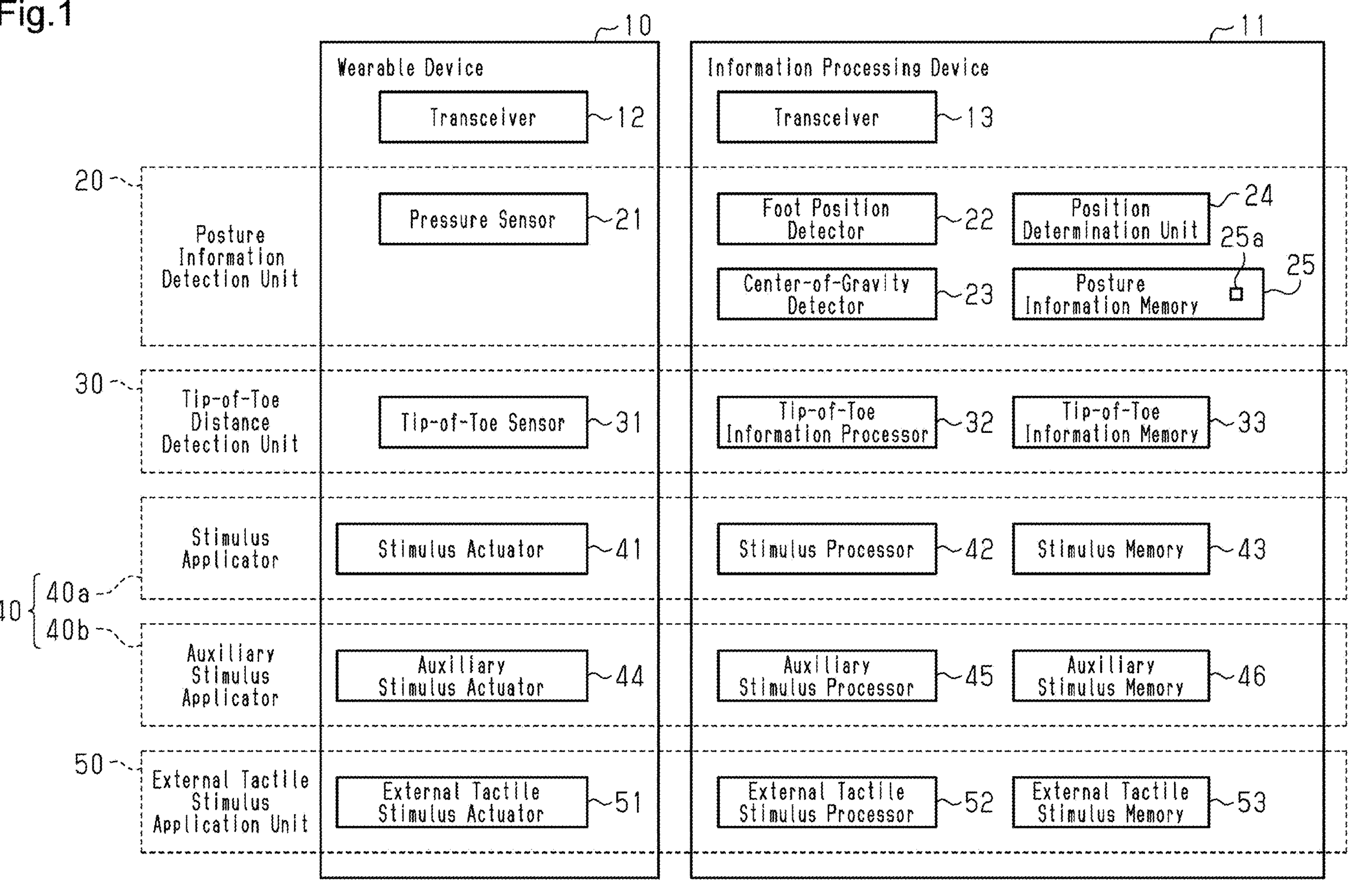
Fig.1
Wearable Device
10
Transceiver
12
Information Processing Device
11
Transceiver
13
20
Posture Information Detection Unit
Pressure Sensor
21
Foot Position Detector
22
Position Determination Unit
24
25a
Center-of-Gravity Detector
23
Posture Information Memory
25
30
Tip-of-Toe Distance Detection Unit
Tip-of-Toe Sensor
31
Tip-of-Toe Information Processor
32
Tip-of-Toe Information Memory
33
Stimulus Applicator
40a
40
40b
Stimulus Actuator
41
Stimulus Processor
42
Stimulus Memory
43
Auxiliary Stimulus Applicator
Auxiliary Stimulus Actuator
44
Auxiliary Stimulus Processor
45
Auxiliary Stimulus Memory
46
50
External Tactile Stimulus Application Unit
External Tactile Stimulus Actuator
51
External Tactile Stimulus Processor
52
External Tactile Stimulus Memory
53

POSTURE CONTROL DEVICE

CROSS-REFERENCE TO RELATED APPLICATIONS

This application is national stage application of International Application No. PCT/JP2022/014074, filed on March 24, 2022, which designates the United States, the entire contents of which is incorporated herein by reference.

TECHNICAL FIELD

The present invention relates to a posture control device.

BACKGROUND

Patent Literature 1 discloses a skin sensory stimulation device that applies skin sensory stimuli to a user based on information related to posture changes output from a detection means capable of detecting changes in the user's posture. By applying skin sensory stimuli to the user, the skin sensory stimulation device of Patent Literature 1 alerts the user to posture changes or induces desired movements.

CITATION LIST

Patent Literature

Patent Literature 1: Japanese Patent No. 4690890

SUMMARY OF INVENTION

Technical Problem

The skin sensory stimulation device of Patent Literature 1 prompts the user to perform actions to maintain posture by making the user aware of posture changes through the application of skin sensory stimuli. However, most actions related to human posture control, such as maintaining posture, are performed unconsciously. There was room for improvement in the ability of the skin sensory stimulation device of Patent Literature 1 to prompt actions related to unconsciously performed posture control.

Solution to Problem

A posture control device that solves the above problem is configured to assist a posture of a user. The posture control device includes a posture information detection unit, a tactile stimulus application unit configured to apply tactile stimuli to somatosensory receptors of the user, and an external tactile stimulus application unit configured to apply external tactile stimuli to the user. The posture information detection unit is configured to detect contact pressures at multiple parts of a sole of the user and detect a change in posture based on temporal changes in the detected contact pressures. The external tactile stimulus application unit is configured to apply the external tactile stimuli to the user, at a specified point in time that is based on a detection result of the posture information detection unit, to assist posture control for the user by integrating the external tactile stimuli with the tactile stimuli applied by the tactile stimulus application unit through sensory integration.

In an aspect of the posture control device, the external tactile stimuli applied by the external tactile stimulus application unit include at least one of auditory stimuli and visual stimuli.

In an aspect of the posture control device, the external tactile stimuli applied by the external tactile stimulus application unit are stimuli delivered through skin of the user.

In an aspect of the posture control device, the external tactile stimulus application unit includes an external tactile stimulus actuator configured to generate external tactile stimuli, and the external tactile stimulus actuator is positioned within a wearable device configured to be worn on a part of a foot beyond an ankle of the user.

In an aspect of the posture control device, the tactile stimulus application unit includes a stimulus applicator configured to apply a vibration to the user, inducing at least one of a response that tenses toes of the user and a response that lifts tips of the toes.

An aspect of the posture control device includes a tip-of-toe distance detector configured to detect a distance between a contact surface and the tips of the toes. The stimulus applicator is configured to provide the user with the vibration that induces the response lifting the tips of the toes at least at one of a first point in time and a second point in time. The first point in time is when the distance between the contact surface and the tips of the toes is less than or equal to a first threshold value at a moment of heel landing. The second point in time is when the distance between the contact surface and the tips of the toes is less than or equal to a second threshold value during a period from a specified time interval after toe off to heel strike.

In an aspect of the posture control device, the tactile stimulus application unit includes an auxiliary stimulus applicator configured to apply tactile stimuli of at least one of weak vibrations and strong vibrations. The weak vibrations amplify tactile signals transmitted from the sole based on stochastic resonance upon ground contact. The strong vibrations induce firing of neural impulses.

An aspect of the posture control device includes a posture determination unit configured to determine whether a gait state is abnormal based on temporal changes in the center of gravity during walking. The temporal changes are calculated from the contact pressures detected by the posture information detection unit. The auxiliary stimulus applicator is configured to apply tactile stimuli to the sole when a determination result of the posture determination unit indicates that the gait state is abnormal.

In an aspect of the posture control device, the posture determination unit is configured to estimate, using a center-of-gravity change model, a part of the sole of the user where the somatosensory receptors are less functional. The center-of-gravity change model is configured to output, in response to an input of the temporal changes in the center of gravity during walking of the user, an estimation result of the part of the sole where the somatosensory receptors are less functional. The auxiliary stimulus applicator is capable of independently applying tactile stimuli to multiple parts of the sole, and is configured to apply tactile stimuli to the part where the posture determination unit has estimated that the somatosensory receptors are less functional.

BRIEF DESCRIPTION OF DRAWINGS

FIG. 1 is a block diagram of a posture control device.

MODES FOR CARRYING OUT THE INVENTION

A posture control device according to an embodiment will now be described.

Posture Control Device

As shown in FIG. 1, the posture control device includes a wearable device 10 configured to be worn by a user, and an information processing device 11.

Figure 2:
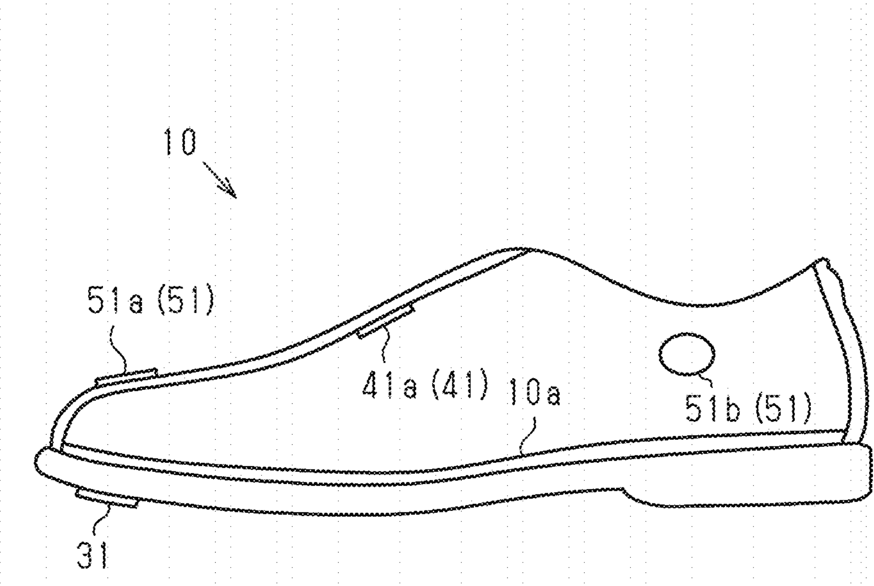
FIG. 2 is a diagram illustrating the wearable device.

The wearable device 10 is a wearable accessory that includes a portion used by wearing it on a part of the foot of the user that is located beyond the ankle. Examples of the wearable device 10 include shoes, socks, and insoles. As shown in FIG. 2, in the present embodiment, an example where the wearable device 10 is a shoe will be described. Examples of the information processing device 11 include a server, a personal computer (PC), a mobile phone such as a smartphone, and a tablet terminal.

As shown in FIG. 1, the wearable device 10 includes a transceiver 12. The information processing device 11 includes a transceiver 13. The transceiver 12 and the transceiver 13 include wired or wireless communication means and perform communicate with each other using a known communication method. Examples of the known communication method include near-field communication such as Bluetooth® communication.

The posture control device includes the following functional components: a posture information detection unit 20, a tip-of-toe distance detection unit 30, a tactile stimulus application unit 40, and an external tactile stimulus application unit 50. These components will now be described in detail.

Posture Information Detection Unit

As shown in FIG. 1, the posture information detection unit 20 includes a pressure sensor 21 that is disposed in the wearable device 10. Further, the posture information detection unit 20 includes a foot position detector 22, a center-of-gravity detector 23, a posture determination unit 24, and a posture information memory 25 that are disposed in the information processing device 11. The foot position detector 22, the center-of-gravity detector 23, and the posture determination unit 24 may be circuitry including: 1) one or more processors that operate according to a computer program (software); 2) one or more dedicated hardware circuits (application specific integrated circuits: ASIC) that execute at least part of various processes; or 3) a combination thereof. The posture information detection unit 20 detects posture information, which indicates changes in user posture, from pressure information detected by the pressure sensor 21.

Pressure Sensor

The pressure sensor 21 is worn on an insole 10*a* of the shoe. The pressure sensor 21 detects the contact pressure applied to the sole of the foot of the user.

Figure 3:
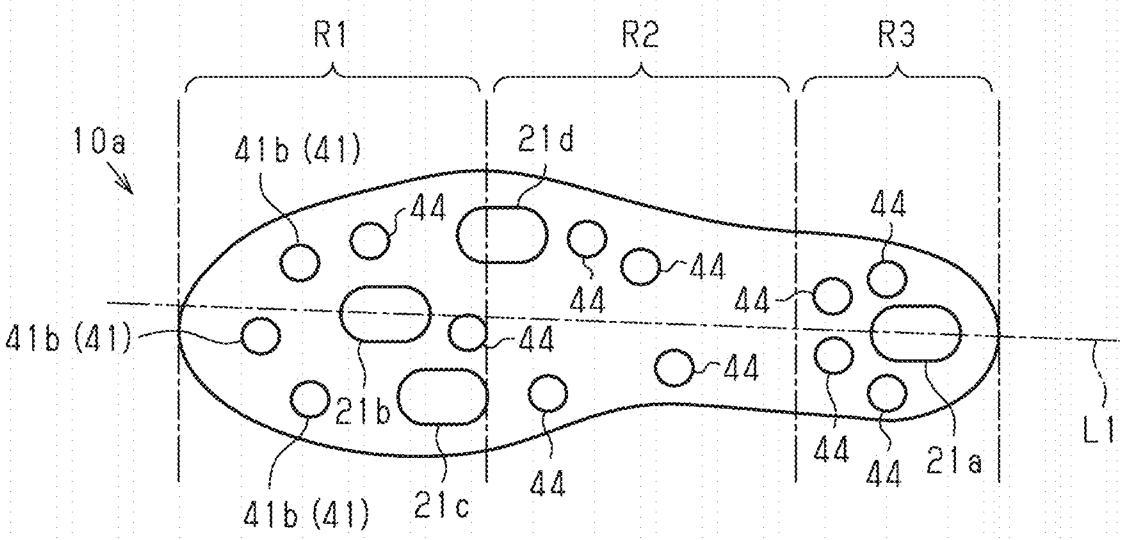
FIG. 3 is a diagram illustrating the arrangement of the pressure sensors, stimulus actuator, and auxiliary stimulus actuator.

As shown in FIG. 3, the pressure sensor 21 includes a heel-side sensor 21*a*, a toe-side sensor 21*b*, an inner-side sensor 21*c*, and an outer-side sensor 21*d*. The heel-side sensor 21*a* is disposed in a portion of the insole 10*a* to which the load of the heel is applied, and detects the pressure applied to the heel of the sole. The toe-side sensor 21*b* is disposed in any portion to which the load of the base of the second to fourth toes is applied, and detects the pressure applied to the toes of the sole. The inner-side sensor 21*c* is disposed on the inner side of line L1 connecting the heel-side sensor 21*a* to the toe-side sensor 21*b* and at a portion to which the load of the ball of the big toe is applied. The inner-side sensor 21*c* detects the pressure applied to the inner part of the sole. The outer-side sensor 21*d* is disposed on the outer side of line L1 and at a portion to which the load of the ball of the little toe is applied. The outer-side sensor 21*d* detects the pressure applied to the outer part of the sole.

In other words, the heel-side sensor 21*a* and the toe-side sensor 21*b* are respectively disposed to detect the pressure at a first position and the pressure at a second position, which are spaced apart from each other in the longitudinal direction on the sole. The inner-side sensor 21*c* and the outer-side sensor 21*d* are respectively disposed to detect the pressure at a third position and the pressure at a fourth position, which are spaced apart from each other in the lateral direction with line L1 connecting the first position to the second position therebetween.

Each of the pressure sensors 21 independently detects the pressure applied to a corresponding part of the sole at specified time intervals. The specified time interval is, for example, 5 to 30 milliseconds. Examples of the pressure sensors 21 include known pressure-sensitive sensors using piezoelectric elements. Particularly, considering the use situation, where the sensors are placed on the soles, it is preferable to use capacitive sensors made of an elastomer that utilizes dielectric elastomer, from the viewpoints of flexibility and durability. Examples of the dielectric elastomer include crosslinked polyrotaxane, silicone elastomer, acrylic elastomer, and urethane elastomer.

Examples of the capacitive sensor made of elastomer include a multilayer structure including sheet-shaped dielectric layers each made of a dielectric elastomer and electrode layers arranged on opposite sides of a corresponding one of the dielectric layers in the thickness direction. When necessary, an insulating layer may be laminated on the outermost layer of the capacitive sensor. The capacitive sensor made of elastomer extends or contracts in response to pressure. This deformation alters the capacitance of the capacitor formed by two electrode layers. By determining the change in capacitance with a detection circuit or the like, the pressure applied to the dielectric elastomer is detected.

The dielectric elastomer of the dielectric layer is not particularly limited, and may be a dielectric elastomer used in a known capacitive sensor. Examples of the dielectric elastomer include crosslinked polyrotaxane, silicone elastomer, acrylic elastomer, and urethane elastomer. One of these types of dielectric elastomer may be used alone, or two or more of these may be used in combination. The thickness of the dielectric layer is, for example, 20 to 200 μm.

Examples of the materials of the electrode layer include conductive elastomer, carbon nanotube, Ketjenblack®, and vapor-deposited metal film. Examples of the conductive elastomer include a conductive elastomer that contains an insulating polymer and a conductive filler.

Examples of the insulating polymer include crosslinked polyrotaxane, silicone elastomer, and urethane elastomer. One of these types of insulating polymer may be used alone, or two or more of these may be used in combination. The conductive filler may be, for example, carbon nanotubes, Ketjenblack®, carbon black, or metal particles of copper, silver, or the like. One of these types of conductive filler may be used alone, or two or more of these may be used in combination. The thicknesses of the positive electrode and the negative electrode are, for example, 1 to 100 μm.

The dielectric elastomer of the insulating layer is not particularly limited, and may be a dielectric elastomer used for an insulating portion of a known capacitive sensor. Examples of the insulating elastomer include crosslinked polyrotaxane, silicone elastomer, acrylic elastomer, and urethane elastomer. One of these types of insulating elastomer may be used alone, or two or more of these may be used in combination. The thickness of the insulating layer is, for example, 10 to 100 μm. The thickness of the capacitive sensor, from the perspective of ensuring flexibility and strength, is preferably, for example, 0.3 to 1.5 mm.

The capacitive sensor made of elastomer preferably includes dielectric elastomers that are crosslinked with polyrotaxane. Specifically, it is preferred that the dielectric layer and the electrode layer are made of dielectric elastomers that are crosslinked with polyrotaxane. In this case, the output curve indicating the change in capacitance in response to a change in pressure applied to the capacitive sensor forms a logarithmic curve. According to the Weber-Fechner law, which states that the magnitude of human perception is proportional to the logarithm of the stimulus strength received, the change in detection sensitivity of the aforementioned capacitive sensor in response to pressure closely approximates human sensory characteristics. Thus, the use of the capacitive sensor provides an output that approximates somatosensory receptors in human skin that sense pressure.

Figure 4:
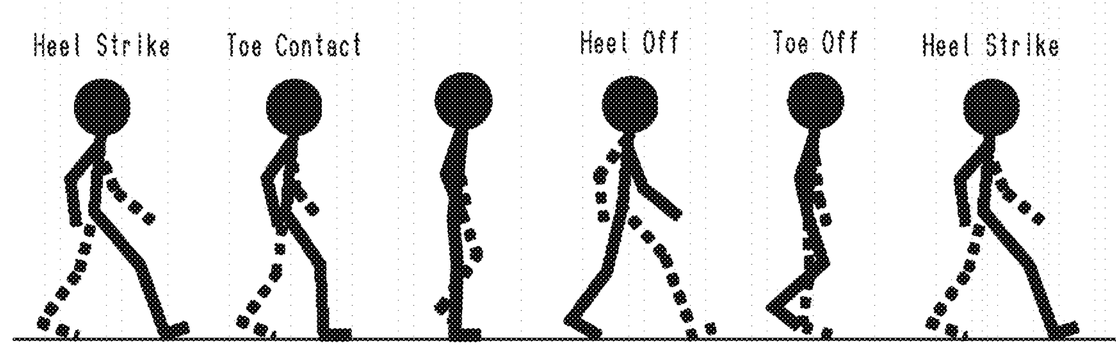
FIG. 4 is a diagram illustrating the gait cycle.

Foot Position Detector, Center-of-Gravity Detector, Posture Determination Unit, and Posture Information Memory The foot position detector 22 calculates the current position of the foot in the gait cycle from changes in pressure information, which are the detected values of the pressure sensor 21. As shown in FIG. 4, in the present embodiment, the gait cycle refers to the period during walking that extends from heel strike, through toe contact and heel off, to toe off. The current foot position within the gait cycle calculated by the foot position detector 22 is posture information, which indicates changes in the user posture. In the following specification, heel strike may be referred to as heel landing, and toe strike may be referred to as toe landing.

Figure 5:
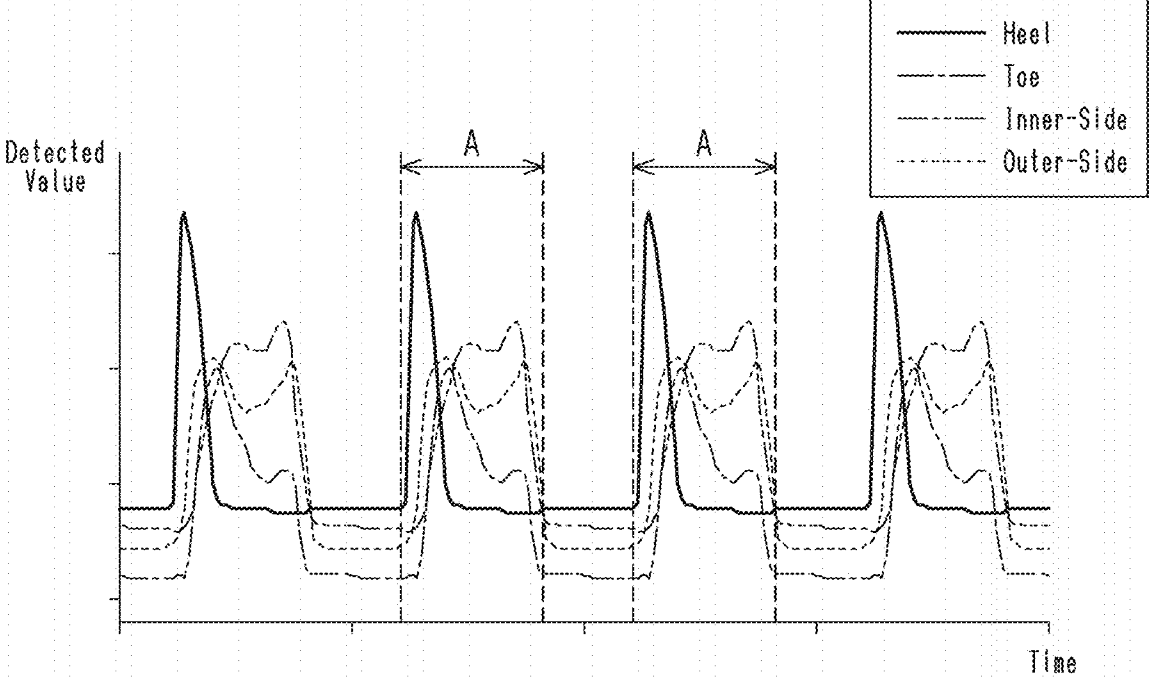
FIG. 5 is waveform data representing temporal changes in detected values at each part of the sole detected by a corresponding pressure sensor.

FIG. 5 is an example of waveform data representing temporal changes in detected values at each part of the sole of one foot detected by a corresponding pressure sensor 21. In FIG. 5, the solid line indicates a detected value of the heel-side sensor 21*a*, the long-dash short-dash line indicates a detected value of the toe-side sensor 21*b*, the long-dash double-short-dash line indicates a detected value of the inner-side sensor 21*c*, and the broken line indicates a detected value of the outer-side sensor 21*d*.

The waveform data obtained during walking periodically repeats an interval in which the pressure value is substantially constant and an interval in which the detected value changes. In the waveform data during walking, the interval in which the detected value is substantially constant is an interval in which the foot is separated from the ground. Section A, in which the detected value changes, is an interval in which the foot is in contact with the ground.

The foot position detector 22 calculates the current position of the foot in the gait cycle from temporal changes in the detected value, which are detected by each pressure sensor 21. For example, the foot position detector 22 determines the point in time of heel contact as the point in time when the detected value of the heel-side sensor 21*a* becomes greater than or equal to a threshold value and determines the point in time of heel off as the point in time when the detected value of the heel-side sensor 21*a* becomes less than or equal to the threshold value. Similarly, the foot position detector 22 determines the point in time of toe contact as the point in time when the detected value of the toe-side sensor 21*b* becomes greater than or equal to a threshold value and determines the point in time of toe off when the detected value of the toe-side sensor 21*b* becomes less than or equal to the threshold value. Instead of the detected values of the pressure sensor 21, the change amount of the detected values of the pressure sensor 21 per unit time may be used to perform determination.

The center-of-gravity detector 23 calculates two-dimensional coordinates of the center of gravity for each detection time interval. X (t) represents the lateral coordinate of the center of gravity at time t, and Y (t) represents the longitudinal coordinate of the center of gravity at time t. The two-dimensional coordinates of the center of gravity pressure can be acquired from the detected values of the four pressure sensors 21 detected during the same detection time interval. The two-dimensional coordinates of the center of gravity detected by the center-of-gravity detector 23 is stored in the posture information memory 25. The two-dimensional coordinates of the center of gravity calculated by the center-of-gravity detector 23 is posture information, which indicates changes in the posture of the user.

The posture determination unit 24 determines whether the gait state of the user is abnormal from the temporal changes in the center of gravity during walking. The posture determination unit 24 makes the determination using a center-of-gravity change model 25*a*, which is stored in the posture information memory 25. The center-of-gravity change model 25*a* is configured to output, in response to an input of the temporal changes in the two-dimensional coordinates of the center of gravity during walking of the user, the estimation result indicating whether the gait state is abnormal and the estimation result for the part of the sole where the somatosensory receptors are less functional. For example, the center-of-gravity change model 25*a* can be constructed by using, as training data, the temporal changes in the two-dimensional coordinates of the center of gravity of a subject during walking, the examination result of the gait state of the subject, and the examination result of the functions of the somatosensory receptors on the sole of the subject.

People who experience instability in posture control while walking tend to exhibit greater oscillation of the center of gravity during walking. Additionally, people having a part of the sole where their somatosensory receptors are less functional tend to walk in a manner that decreases or increases the load on the part where the somatosensory receptors are less functional, resulting in a characteristic change in the center of gravity over time. The center-of-gravity change model 25*a* utilizes this tendency.

The posture information memory 25 stores the acquired pressure information and the two-dimensional coordinates of the center of gravity. The posture information memory 25 also stores an execution program for controlling execution of the center-of-gravity change model 25*a* and execution of the processes in the foot position detector 22, the center-of-gravity detector 23, and the posture determination unit 24.

Tip-of-Toe Distance Detection Unit

As shown in FIG. 1, the tip-of-toe distance detection unit 30 includes a tip-of-toe sensor 31 that is disposed in the wearable device 10. Further, the tip-of-toe distance detection unit 30 includes a tip-of-toe information processor 32 and a tip-of-toe information memory 33 that are disposed in the information processing device 11. The tip-of-toe information processor 32 may be circuitry including: 1) one or more processors that operate according to a computer program (software); 2) one or more dedicated hardware circuits (application specific integrated circuits: ASIC) that execute at least part of various processes; or 3) a combination thereof. From the position information of the tips of the toe detected by the tip-of-toe sensor 31, the tip-of-toe distance detection unit 30 calculates the distance between the contact surface and the tips of the toes at points in the gait cycle, and determines whether the user is in a state that may induce a fall.

Tip-of-Toe Sensor

The tip-of-toe sensor 31 detects the position of the tips of the toes of the user. The tip-of-toe sensor 31 is mounted at a position corresponding to the tips of the toes in the sole of the shoe, which is the wearable device 10.

The tip-of-toe sensor 31 detects, without contact, a detected value indicating the distance between the contact surface and the tips of the toes at specified time intervals. The specified time interval is, for example, 5 to 30 milliseconds. Examples of the tip-of-toe sensor 31 include a known non-contact sensor, such as an optical sensor with a light emitting element and a light receiving element.

Tip-of-Toe Information Processor and Tip-of-Toe Information Memory

The tip-of-toe information memory 33 stores an execution program for controlling the execution of each process in the tip-of-toe information processor 32.

The tip-of-toe information processor 32 calculates the distance between the tips of the toe and the contact surface at specified points in the gait cycle, from the calculation results of the foot position detector 22 and the detected values detected by the tip-of-toe sensor 31. Then, the tip-of-toe information processor 32 determines that the user is in a fall-inducing state, indicating a high risk of tripping, when the distance between the contact surface and the tips of the toes meets the following conditions 1 and 2. Condition 1 is that the distance between the contact surface and the tips of the toes at a moment of heel landing is less than or equal to a preset first threshold value. Condition 2 is that the distance between the contact surface and the tips of the toes and is less than or equal to a second threshold value during a period from a specified time interval after toe off to heel strike. The first threshold value, second threshold value, and specified time interval may be set to any value. The specified time interval corresponds to, for example, a duration that is 50% to 90% of the duration required from the previous toe off to the previous heel contact.

Tactile Stimulus Application Unit

As shown in FIG. 1, the tactile stimulus application unit 40 includes a stimulus applicator 40*a* that applies stimuli to the somatosensory receptors of the user and an auxiliary stimulus applicator 40*b* that applies sensory auxiliary stimuli to the receptors.

Stimulus Applicator

The stimulus applicator 40*a* includes a stimulus actuator 41 that is disposed in the wearable device 10. The stimulus applicator 40*a* further includes a stimulus processor 42 and a stimulus memory 43 that are disposed in the information processing device 11. The stimulus processor 42 may be circuitry including: 1) one or more processors that operate according to a computer program (software); 2) one or more dedicated hardware circuits (application specific integrated circuits: ASIC) that execute at least part of various processes; or 3) a combination thereof. The stimulus applicator 40*a* applies stimuli to the user through the vibration of the stimulus actuator 41 based on control signals that are output from the stimulus processor 42.

Stimulus Actuator

The stimulus actuator 41 is a vibrator that induces a response that causes muscle contraction by vibrating a specific part of the user. The posture control device assists user posture control by utilizing reflex actions based on the response induced by the user foot due to the vibration of the stimulus actuator 41.

Examples of responses induced to assist the user posture control include a response that causes muscle contraction in the direction of lifting the tips of the toes and a response that tenses the toes to maintain force in the toes.

The placement of the stimulus actuator 41 in the shoe, which is the wearable device 10, is set according to the type of response to be induced. When the induced response causes muscle contraction in the direction of lifting the tips of the toes, the stimulus actuator 41 is positioned on the part of the inner surface of the shoe that is in contact with the instep. When the induced response causes the toes to tense, the stimulus actuator 41 is positioned on the part of the insole 10*a* of the shoe that is in contact with the balls of the toes.

In the present embodiment, as an example, the configuration that induces a response causing muscle contraction in the direction of lifting the tips of the toes and a response that tenses the toes, will be described. As shown in FIG. 2, the wearable device 10 includes a stimulus actuator 41*a* as the stimulus actuator 41 that induces a response causing muscle contraction in the direction of lifting the tips of the toes. The stimulus actuator 41*a* is positioned on the part of the inner surface of the shoe that is in contact with the instep. As shown in FIG. 3, the wearable device 10 includes a stimulus actuator 41*b* as the stimulus actuator 41 that induces a response causing the toes to tense. The stimulus actuator 41*b* is positioned on the part of the insole 10*a* of the shoe that is in contact with the balls of the toes.

The vibrator of the stimulus actuator 41 is not particularly limited if it can apply the desired vibration. Examples of the vibrator include other types of electroactive polymer actuators (EPA) such as a sheet-shaped dielectric elastomer actuator (DEA) and an ionic polymer metal composite (IPMC), an eccentric motor, a linear resonant actuator, a voice coil actuator, and a piezoelectric actuator. The stimulus actuator 41 includes a driving unit (not shown) that applies voltage to the stimulus actuator 41 from a power source, such as a battery (not shown).

The stimulus actuator 41 preferably uses a sheet-shaped DEA as the vibrator. The DEA vibrates based on its deformation, such as stretching and contracting, in response to a user touching its surface. The DEA is, for example, a multilayer structure that includes sheet-shaped dielectric layers, each made of a dielectric elastomer, along with positive electrode layers and negative electrode layers. Each dielectric layer has a positive electrode layer on one side and a negative electrode layer on the opposite side in the thickness direction. If necessary, an insulating layer is laminated on the outermost layer of the DEA. In the DEA, when direct-current voltage is applied across the positive electrode and the negative electrode, the dielectric layer is deformed so as to be compressed in the thickness direction and to be extended in the planar direction of the DEA, which is a direction along the plane of the dielectric layer, in accordance with the magnitude of the applied voltage.

The dielectric elastomer of the dielectric layer is not particularly limited and may be dielectric elastomer used for a known DEA. Examples of the dielectric elastomer include crosslinked polyrotaxane, silicone elastomer, acrylic elastomer, and urethane elastomer. One of these types of dielectric elastomer may be used alone, or two or more of these may be used in combination. The thickness of the dielectric layer is, for example, 20 to 200 μm.

Examples of the materials of the electrode layer include conductive elastomer, carbon nanotube, Ketjenblack®, and vapor-deposited metal film. Examples of the conductive elastomer include a conductive elastomer that contains an insulating polymer and a conductive filler.

Examples of the insulating polymer include crosslinked polyrotaxane, silicone elastomer, and urethane elastomer. One of these types of insulating polymer may be used alone, or two or more of these may be used in combination. The conductive filler may be, for example, carbon nanotubes, Ketjenblack®, carbon black, or metal particles of copper, silver, or the like. One of these types of conductive filler may be used alone, or two or more of these may be used in combination. The thicknesses of the positive electrode and the negative electrode are, for example, 1 to 100 μm.

The dielectric elastomer of the insulating layer is not particularly limited and may be a dielectric elastomer used for an insulating portion of a known DEA. Examples of the insulating elastomer include crosslinked polyrotaxane, silicone elastomer, acrylic elastomer, and urethane elastomer. One of these types of insulating elastomer may be used alone, or two or more of these may be used in combination. The thickness of the insulating layer is, for example, 10 to 100 μm. The thickness of the DEA, from the perspective of ensuring flexibility and strength, is preferably, for example, 0.5 to 1.5 mm.

Stimulus Processor and Contraction Stimulus Memory

The stimulus memory 43 stores an execution program for controlling the execution of each process in the stimulus processor 42.

The stimulus processor 42 controls the action of the stimulus actuator 41. The stimulus processor 42 receives the current position of the foot calculated by the foot position detector 22, the determination result of the tip-of-toe distance detection unit 30, and the determination result of the posture determination unit 24.

At a point in time when the tip-of-toe distance detection unit 30 determines that the fall-inducing state is present, the stimulus processor 42 outputs a control signal to the stimulus actuator **41*a* to make it vibrate in the direction of inducing a response causing muscle contraction and lifting the tips of the toes. Thus, the stimulus applicator 40*a*** applies vibrations to the user, inducing a response that lifts the tips of the toes at least at one of a first point in time and a second point in time. The first point in time is when the distance between the contact surface and the tips of the toes at the moment of heel strike is less than or equal to the first threshold value. The second point in time is when the distance between the contact surface and the tips of the toes is less than or equal to the second threshold value during the period from a specified time interval after toe off to heel strike.

When foot muscles are less functional, the tips of the toes may land before the heel during walking, increasing the risk of tripping. The response induced by the stimulus applicator **40*a*** lifts the tips of the toes at a specified point in time, thereby reducing the risk of the user tripping. Additionally, the response guides the user to walk by landing the heel first, followed by the tips of the toes.

At the point in time when the posture determination unit 24 determines that the posture control is unstable during walking of the user, the stimulus processor 42 outputs a control signal to the stimulus actuator **41*a*** to make it vibrate in the direction of inducing a response that tenses the toes at least at one of the point in time of the heel landing and the point in time of the toe landing. This makes the toes tense, thereby enhancing the gripping force of the toes when they contact the ground. As a result, the soles of the user more effectively support their body weight.

Auxiliary Stimulus Applicator

The auxiliary stimulus applicator **40*b* includes an auxiliary stimulus actuator 44 disposed in the wearable device 10. The auxiliary stimulus applicator 40*b* further includes an auxiliary stimulus processor 45 and an auxiliary stimulus memory 46 that are disposed in the information processing device 11. The auxiliary stimulus processor 45 may be circuitry including: 1) one or more processors that operate according to a computer program (software); 2) one or more dedicated hardware circuits (application specific integrated circuits: ASIC) that execute at least part of various processes; or 3) a combination thereof. The auxiliary stimulus applicator 40*b* applies auxiliary sensory stimuli to the user through the vibration of the auxiliary stimulus actuator 44 based on control signals that are output from the auxiliary stimulus processor 45**.

Auxiliary Stimulus Actuator

The auxiliary stimulus actuator 44 is a vibrator that applies vibrations to the sole of the user to enhance or complement the sensitivity of the somatosensory receptors in the sole. The posture control device assists user posture control by enhancing or complementing the functions of the somatosensory receptors in the sole of the user through the vibrations of the auxiliary stimulus actuator 44.

The auxiliary stimulus actuator 44 is capable of applying two types of vibrations to the sole of the user. The first vibration applied by the auxiliary stimulus actuator 44 is a weak vibration with an intensity that is less than or equal to a threshold value detectable by somatosensory receptors. The weak vibration applied to the sole of the user by the auxiliary stimulus actuator 44 amplifies the tactile signals transmitted from the somatosensory receptors in the user sole through stochastic resonance. This improves the sensitivity of the somatosensory receptors in the sole of the user. Stochastic resonance occurs when adding noise to a signal amplifies the signal and improves response under a specific probability. The second vibration applied by the auxiliary stimulus actuator 44 is a strong vibration that induces the firing of nerve impulses. The second vibration is stronger than the weak vibration. This strong vibration, for example, applies a stimulus with an intensity ranging from 22 to 257 mN in the direction normal to the sole of the foot. The strong vibration applied to the sole of the user by the auxiliary stimulus actuator 44 is applied to somatosensory receptors with significantly reduced functions, thereby inducing the firing of nerve impulses from the somatosensory receptors. This complements the reduced functions of the somatosensory receptors.

As shown in FIG. 3, one or more auxiliary stimulus actuators 44 are arranged in the insole 10*a* within each of a toe region R1, a middle region R2, and a heel region R3 of the sole. The toe region R1 is the region of the sole located in front of the front end of the arch of the foot. The heel region R3 is the region of the sole located behind the rear end of the arch of the foot. The middle region R2 is located between the toe region R1 and the heel region R3. The number and arrangement of the auxiliary stimulus actuators are not particularly limited. It is preferred that two or more auxiliary stimulus actuators 44 be arranged in a distributed manner in each of the toe region R1, middle region R2, and heel region R3.

The vibrator of the auxiliary stimulus actuator 44 is not particularly limited if it can apply the desired vibration. This vibrator may be the same as the example of the vibrator of the stimulus actuator 41. The auxiliary stimulus actuator 44 includes a driving unit (not shown) that applies voltage to the auxiliary stimulus actuator 44 from a power source, such as a battery (not shown).

Auxiliary Stimulus Processor and Auxiliary Stimulus Memory

The auxiliary stimulus memory 46 stores an execution program for controlling the execution of each process in the auxiliary stimulus processor 45.

The auxiliary stimulus processor 45 independently controls the action of each auxiliary stimulus actuator 44. The auxiliary stimulus processor 45 continuously outputs control signals to the auxiliary stimulus actuators 44 to vibrate them such that they constantly apply weak vibrations to the user while the user is wearing the wearable device 10.

The auxiliary stimulus processor 45 receives the current position of the foot calculated by the foot position detector 22 and the determination result of the posture determination unit 24. Immediately after the determination, the auxiliary stimulus processor 45 receives the determination result of the posture determination unit 24. When receiving the estimation result of the part where the somatosensory receptors on the sole are less functional from the posture determination unit 24, the auxiliary stimulus processor 45 outputs control signals to the auxiliary stimulus actuators 44 to vibrate them, applying strong vibrations to the user that induce the firing of nerve impulses.

In this situation, the auxiliary stimulus processor 45 controls a specific auxiliary stimulus actuator 44 that is located relatively near the part of the sole indicated by the estimation result of the posture determination unit 24 such that strong vibrations are applied to that auxiliary stimulus actuator 44 instead of the above weak vibrations. The period for applying strong vibrations may be set to any value. This period refers to the period until the user performs a deactivation operation or the period until a preset time interval elapses. After the period for applying strong vibrations ends, the auxiliary stimulus processor 45 controls the specific auxiliary stimulus actuator 44 to apply weak vibrations instead of strong vibrations.

External Tactile Stimulus Application Unit

As shown in FIG. 1, the external tactile stimulus application unit 50 includes an external tactile stimulus actuator 51 that is disposed in the wearable device 10. The external tactile stimulus application unit 50 further includes an external tactile stimulus processor 52 and an external tactile stimulus memory 53 that are disposed in the information processing device 11. The external tactile stimulus processor 52 may be circuitry including: 1) one or more processors that operate according to a computer program (software); 2) one or more dedicated hardware circuits (application specific integrated circuits: ASIC) that execute at least part of various processes; or 3) a combination thereof. The external tactile stimulus application unit 50 applies external tactile stimuli to the user through the vibration of the external tactile stimulus actuator 51 based on control signals that are output from the external tactile stimulus processor 52.

External Tactile Stimulus Actuator

The external tactile stimulus actuator 51 provides the user with external tactile stimuli, which are received by sensory receptors responsible for senses other than touch. Examples of the external tactile stimuli include auditory stimuli, visual stimuli, olfactory stimuli, gustatory stimuli, and stimuli to somatosensory receptors other than touch. Examples of the stimuli to somatosensory receptors other than touch include superficial sensations (e.g., thermal stimuli and electrical stimuli). Instead, the external tactile stimuli may be stimuli transmitted through deep sensation, such as auditory stimuli using bone conduction. Among these, it is preferable for the external tactile stimuli to include at least one of auditory stimuli and visual stimuli. Preferably, the external tactile stimuli are stimuli delivered through the skin, similar to auditory stimuli using bone conduction.

In addition, the external tactile stimuli applied by the external tactile stimulus actuator 51 may be of a single type or a combination of two or more different types. In other words, the posture control device may apply two different types of sensory stimuli, including the tactile stimuli applied by the tactile stimulus application unit 40, or may apply three or more different types of sensory stimuli.

Examples of the external tactile stimulus actuator 51 include a light emitter, a sound emitter, a heat generator, and an electrical stimulus generator. In the present embodiment, as an example, the external tactile stimulus actuator 51 will be described in a case where it includes a light emitter 51*a* for visual stimulation and a sound generator 51*b* for auditory stimulation via bone conduction. As shown in FIG. 2, the light emitter 51*a* is positioned on the upper surface of the shoe, which is the wearable device 10, such that the light emitted from the light emitter 51*a* enters the user's field of view. The sound generator 51*b*, which uses bone conduction for auditory stimulation, is positioned at the part of the inner surface of the shoe that is in contact with the area around the ankle.

External Tactile Stimulus Processor and External Tactile Memory

The external tactile stimulus memory 53 stores an execution program for controlling the execution of each process in the external tactile stimulus processor 52.

The external tactile stimulus processor 52 controls the action of the external tactile stimulus actuator 51. Human posture control is not only based on the input of tactile stimuli applied to the soles. For human posture control, the central nervous system causes the received tactile stimuli to be integrated through sensory integration with external tactile stimuli, such as visual and auditory stimuli, that are received together with the tactile stimuli. Then, actions to control posture are performed based on the integrated sensory information.

The external tactile stimulus processor 52 outputs control signals to the external tactile stimulus actuator 51 to cause the external tactile stimulus actuator 51 to provide external tactile stimuli to the user, thereby assisting in posture control. The external tactile stimuli applied by the external tactile stimulus processor 52 is integrated through sensory integration with the sense of the tactile stimuli applied to the sole of the user during walking. The external tactile stimuli favorably affect the action to control the posture based on the integrated sensory information.

The details of the external tactile stimuli applied to the user by the external tactile stimulus actuator 51, including the type of external tactile stimuli, the magnitude of output, and the point in time of applying external tactile stimuli are individually set according to the state of the user posture control. In other words, an examination is conducted for the user to measure the current state of posture control. Based on the examination result, the details of external tactile stimuli suitable for improving the posture control state.

The external tactile stimulus processor 52 controls the external tactile stimulus actuator 51 such that the external tactile stimuli corresponding to the details of the set external tactile stimuli are applied. The details of the set external tactile stimuli are pre- written in the execution programs stored in the external tactile stimulus memory 53.

For example, assume user A is diagnosed as having instable posture control during the above examination for the current state of posture control, the instability being attributed to a deficiency in tactile stimulus signals applied to the soles due to reduced functions of the somatosensory receptors. User A, during walking, perceives still being in the process of landing even when the soles have firmly contacted the ground. As a result, user A is unable to properly perform the necessary actions associated with landing during walking, leading to instability in their gait.

To user A, it is preferable to apply external tactile stimuli that enhance the perception of landing when the feet contact the ground. Examples of the external tactile stimuli that enhance the perception of landing when the feet contact the ground include external tactile stimuli that intensify the tactile signals applied to the soles of user A. By applying external tactile stimuli that intensify the tactile signals during landing, the external tactile stimulus application unit 50 enables user A to more strongly perceive the sensation of landing. This stabilizes the posture control for user A.

In this case, the external tactile stimuli that intensify the signals of tactile stimuli applied to the sole of user A are explored and determined. Next, the intensity at which the signals of the tactile stimuli applied to the sole are suitable for the determined external tactile stimuli is determined. These tasks are performed to determine the details of the external tactile stimuli suitable for stabilizing the posture control for user A.

Another example of the external tactile stimuli that enhance the perception of landing when contacting the ground is stimuli that substitute for or supplement the tactile sensation of landing. For example, during walking, the details of the external tactile stimuli are set so that constant external tactile stimuli, such as sound or light, are generated with each landing. In this case, as a result of the repeated input of constant external tactile stimuli with each landing during walking, user A will begin to perceive the point in time of receiving the external tactile stimuli as the point in time of landing, or they will start to predict the point in time of landing. In this manner, the sense of landing based on the tactile perception of user A is substituted for or supplemented by external tactile stimuli, enabling user A to perceive or predict the point in time of the landing. This stabilizes the posture control for user A.

The operation and advantages of the posture control device according to the present embodiment will now be described.

(1) The posture control device includes the posture information detection unit 20, the tactile stimulus application unit 40, which is configured to apply tactile stimuli to the somatosensory receptors of the user, and the external tactile stimulus application unit 50, which is configured to apply external tactile stimuli to the user. The posture information detection unit 20 is configured to detect the contact pressures at multiple parts of the sole and detect a change in posture based on temporal changes in the detected contact pressures. The external tactile stimulus application unit 50 is configured to apply external tactile stimuli to the user, at a specified point in time that is based on the detection result of the posture information detection unit 20, to assist the user posture control by integrating external tactile stimuli with tactile stimuli applied by the tactile stimulus application unit 40 through sensory integration.

In this configuration, tactile stimuli and external tactile stimuli, which are delivered from different sensory systems, are combined and applied to the user. For user posture control, adjustment is made such that the external tactile stimuli applied to the user are integrated with the tactile stimuli applied by the tactile stimulus application unit 40 through sensory integration. By applying tactile stimuli and external tactile stimuli, integrated through sensory integration for posture control, to the user at appropriate points in time, it is possible to intervene in the unconscious posture control of the user and promote specific actions based on this unconscious posture control. As a result, diverse and effective assistance are provided to stabilize the user posture, tailored to their posture control state.

(2) The external tactile stimuli applied by the external tactile stimulus application unit 50 is at least one of auditory stimuli and visual stimuli.

Among external tactile stimuli, visual and auditory stimuli are particularly easily integrated with tactile stimuli through sensory integration for human posture control, thus having a significant impact on posture control. Thus, when auditory and visual stimuli are applied, it is easier to adjust and stabilize the user posture control compared to when other external tactile stimuli are applied.

(3) The external tactile stimuli applied by the external tactile stimulus application unit 50 are delivered through the skin.

This configuration allows the external tactile stimulus actuator 51 of the external tactile stimulus application unit 50, which generates external tactile stimuli, to be mounted in unnoticeable positions such as inside clothing.

(4) The external tactile stimulus application unit 50 includes the external tactile stimulus actuator 51, which is configured to generate external tactile stimuli. The external tactile stimulus actuator 51 is positioned within the wearable device 10, which is configured to be worn on the part of the foot beyond the ankle of the user.

In this configuration, the only device the user needs to wear is the wearable device 10 for the foot. This simplifies the required wearing procedure for the user. The device worn by the user does not obstruct their eyes or ears. Thus, the posture control device does not hinder the acquisition of external tactile information or auditory information that are normally obtained from outside.

(5) The tactile stimulus application unit 40 includes the stimulus applicator 40*a*, which is configured to apply a vibration to the user, inducing a response that tenses the toes.

This configuration enhances the gripping force of the toes when contacting the ground. As a result, the soles of the user more effectively support their body weight. Consequently, the landing posture is stabilized.

(6) The tactile stimulus application unit 40 includes the stimulus applicator 40*a*, which is configured to apply a inducing vibration to the user, inducing a response that lifts the tips of the toes.

This configuration prevents tripping caused by insufficient lift of the tips of the toes. Consequently, the walking posture is stabilized.

(7) The posture control device includes the tip-of-toe distance detection unit 30, which is configured to detect the distance between the contact surface and the tips of the toes. The stimulus applicator 40*a* applies vibrations to the user, inducing a response that lifts the tips of the toes, at least at one of the first point in time and the second point in time. The first point in time is when the distance between the contact surface and the tips of the toes at the moment of heel strike is less than or equal to the first threshold value. The second point in time is when the distance between the contact surface and the tips of the toes is less than or equal to the second threshold value during the period from the specified time interval after toe off to heel strike.

This configuration guides the user to walk by landing the heel first, followed by the tips of the toes.

(8) The tactile stimulus application unit 40 includes the auxiliary stimulus applicator 40*b*, which is configured to apply weak vibrations that intensify, upon ground contact, tactile signals transmitted from the sole based on stochastic resonance.

This configuration intensifies the tactile signals transmitted from the somatosensory receptors in the sole through stochastic resonance. This improves the state in which posture control is unstable due to weak or insufficient tactile signals necessary for posture control.

(9) The tactile stimulus application unit 40 includes the auxiliary stimulus applicator 40*b*, which is configured to apply strong vibrations that induce the firing of neural impulses to the sole.

In this configuration, the strong vibrations applied by the auxiliary stimulus applicator 40*b* complements the reduced functions of the somatosensory receptors. This improves the state in which posture control is unstable due to the reduced functions of the somatosensory receptors.

(10) The posture control device includes the posture determination unit 24, which is configured to determine whether the gait state is abnormal based on temporal changes in the center of gravity during walking. The temporal changes are calculated from the contact pressure detected by the posture information detection unit 20. The auxiliary stimulus applicator 40*b* is configured to apply tactile stimuli to the sole when the determination result of the posture determination unit 24 indicates that the gait state is abnormal.

This configuration allows the auxiliary stimulus applicator 40*b* to apply tactile stimuli at appropriate points in time. Accordingly, the unnecessary application of tactile stimuli is prevented.

(11) The posture determination unit 24 is configured to estimate the part of the sole of the user where the somatosensory receptors are less functional, using the center-of-gravity change model 25*a*. The center-of-gravity change model 25*a* is configured to output the estimation result of the part of the sole of the user, where the somatosensory receptors are less functional, in response to an input of temporal changes in the center of gravity during walking of the user. The auxiliary stimulus applicator 40*b* is capable of independently providing tactile stimuli to multiple parts of the sole, and is configured to apply tactile stimuli to the part where the posture determination unit 24 has estimated that the somatosensory receptors are less functional.

This configuration allows the auxiliary stimulus applicator 40*b* to locally apply tactile stimuli to parts that need assistance. In other words, the parts with reduced somatosensory receptor functions are assisted effectively.

The present embodiment may be modified as follows. The present embodiment and the following modifications can be combined as long as they remain technically consistent with each other.

The posture control device may include a second wearable device that is worn on a part of the user body other than the foot beyond the ankle. The external tactile stimulus actuator 51 is disposed in the second wearable device. The second wearable device in which the external tactile stimulus actuator 51 applies auditory stimuli is, for example, a wearable accessory such as an earphone worn on the ear. The second wearable device in which the external tactile stimulus actuator 51 applies visual stimuli is, for example, a wearable accessory such as glasses worn on the face. There may be one or more types of second wearable devices.

The information processing device 11 may be incorporated in the wearable device 10.

In the above embodiment, the auxiliary stimulus applicator 40*b* constantly applies weak vibrations to the user during the entire period in which the wearable device 10 is worn. Instead, the auxiliary stimulus applicator 40*b* may apply weak vibrations during specific periods at specific points in time. For example, in the same manner as strong vibrations that induce the firing of neural impulses, weak vibrations may be applied when the estimation result of the part where the part of the sole with reduced somatosensory receptor functions is received from the posture determination unit 24.

Instead of applying weak vibrations from all of the auxiliary stimulus actuators 44, the auxiliary stimulus applicator 40*b* may apply weak vibrations only to a specific part of the sole. For example, when the estimation result of the part where the part of the sole with reduced somatosensory receptor functions is received, weak vibrations are applied only from a specific auxiliary stimulus actuator 44 that is relatively near a part of the sole indicated by the estimation result of the posture determination unit 24.

In the above embodiment, the part of the sole with reduced somatosensory receptor functions is estimated. Instead, the part of the user sole with reduced somatosensory receptor functions may be identified in advance, and then, one or both of weak vibrations and strong vibrations may be applied to the identified part.

The auxiliary stimulus applicator 40*b* may be configured to apply only one of weak vibration and strong vibration that induce the firing of neural impulses.

One of the stimulus applicator 40*a* and the auxiliary stimulus applicator 40*b* may be omitted.

The posture control device may include a model generator that produces a pre-trained stimulation model. This model is constructed through machine learning based on input-output patterns reflecting the state of user posture control. In this case, the tactile stimulus application unit 40 and the external tactile stimulus application unit 50 preferably use a stimulus application model generated by the model generator to determine the details of the tactile stimuli to be applied and the details of the external tactile stimuli to be applied.

For example, a memory is provided to store the details of the tactile stimuli applied by the tactile stimulus application unit 40 and the external tactile stimuli applied by the external tactile stimulus application unit 50 for one user. The memory also stores the data of two-dimensional coordinates of the foot position and the center of gravity during application of the tactile stimuli and external tactile stimuli. The stimulus application model is configured to learn the data stored in the memory. Further, the model is configured to output, to the received two-dimensional coordinates of the center of gravity, the details of the tactile stimuli applied by the tactile stimulus application unit 40 and the details of the external tactile stimuli applied by the external tactile stimulus application unit 50 that are suitable for stabilizing posture control.

The state of the posture that can be assisted by the posture control device is not limited to the gait state. The posture state only needs to be a state in which posture control is performed based on tactile stimuli added to the sole. For example, the posture control device may assist the user posture during static standing.

The invention claimed is:

1. A posture control device configured to assist a posture of a user, the posture control device comprising:

a posture information detection unit;

a tactile stimulus application unit configured to apply tactile stimuli to somatosensory receptors of the user; and an external tactile stimulus application unit configured to apply external tactile stimuli other than touch to the user, wherein the posture information detection unit is configured to detect contact pressures at multiple parts of a sole of the user and detect a change in posture based on temporal changes in the detected contact pressures, and the external tactile stimulus application unit is configured to apply the external tactile stimuli to the user, at a specified point in time that is based on a detection result of the posture information detection unit, to assist posture control for the user by integrating the external tactile stimuli with the tactile stimuli applied by the tactile stimulus application unit through sensory integration.

2. The posture control device according to claim 1, wherein the external tactile stimuli applied by the external tactile stimulus application unit include at least one of auditory stimuli and visual stimuli.

3. The posture control device according to claim 1, wherein the external tactile stimuli applied by the external tactile stimulus application unit are stimuli delivered through skin of the user.

4. The posture control device according to claim 1, wherein the external tactile stimulus application unit includes an external tactile stimulus actuator configured to generate external tactile stimuli, and the external tactile stimulus actuator is positioned within a wearable device configured to be worn on a part of a foot beyond an ankle of the user.

5. The posture control device according to claim 1, wherein the tactile stimulus application unit includes an auxiliary stimulus applicator configured to apply tactile stimuli of at least one of weak vibrations and strong vibrations, wherein the weak vibrations amplify tactile signals transmitted from the sole based on stochastic resonance upon ground contact, and the strong vibrations induce firing of neural impulses.

6. The posture control device according to claim 5, further comprising a posture determination unit configured to determine whether a gait state of the user is abnormal based on temporal changes in the center of gravity during walking, the temporal changes being calculated from the contact pressures detected by the posture information detection unit, wherein the auxiliary stimulus applicator is configured to apply tactile stimuli to the sole when a determination result of the posture determination unit indicates that the gait state is abnormal.

7. The posture control device according to claim 6, wherein the posture determination unit is configured to estimate, using a center-of-gravity change model, a part of the sole of the user where the somatosensory receptors are less functional, wherein the center-of-gravity change model is configured to output, in response to an input of the temporal changes in the center of gravity during walking of the user, an estimation result of the part of the sole where the somatosensory receptors are less functional, and the auxiliary stimulus applicator is capable of independently providing tactile stimuli to multiple parts of the sole, and is configured to apply tactile stimuli to the part where the posture determination unit has estimated that the somatosensory receptors are less functional.

8. The posture control device according to claim 1, wherein the external tactile stimuli is different than the tactile stimuli.

9. A posture control device configured to assist a posture of a user, the posture control device comprising:

a posture information detection unit;

a tactile stimulus application unit configured to apply tactile stimuli to somatosensory receptors of the user; and an external tactile stimulus application unit configured to apply external tactile stimuli to the user, wherein the posture information detection unit is configured to detect contact pressures at multiple parts of a sole of the user and detect a change in posture based on temporal changes in the detected contact pressures, and the external tactile stimulus application unit is configured to apply the external tactile stimuli to the user, at a specified point in time that is based on a detection result of the posture information detection unit, to assist posture control for the user by integrating the external tactile stimuli with the tactile stimuli applied by the tactile stimulus application unit through sensory integration, wherein the tactile stimulus application unit includes a stimulus applicator configured to apply a vibration to the user, inducing at least one of a response that tenses toes of the user and a response that lifts tips of the toes.

10. The posture control device according to claim 9, further comprising a tip-of-toe distance detector configured to detect a distance between a contact surface and the tips of the toes, wherein the stimulus applicator is configured to provide the user with the vibration that induces the response lifting the tips of the toes at least at one of a first point in time and a second point in time, the first point in time is when the distance between the contact surface and the tips of the toes is less than or equal to a first threshold value at a moment of heel landing, and the second point in time is when the distance between the contact surface and the tips of the toes is less than or equal to a second threshold value during a period from a specified time interval after toe off to heel strike.

11. A computer program product for a posture control device configured to assist a posture of a user, the computer program product comprising a non-transitory computer readable medium including computer program instructions causing the computer to execute:

detecting a posture information comprising detecting contact pressures at multiple parts of a sole of the user and detect a change in posture based on temporal changes in the detected contact pressures;

applying tactile stimuli to somatosensory receptors of the user; and applying external tactile stimuli to the user including applying the external tactile stimuli to the user, at a specified point in time that is based on a detection result of the posture information detection unit, to assist posture control for the user by integrating the external tactile stimuli with the tactile stimuli applied by the tactile stimulus application unit through sensory integration.

12. The computer program product according to claim 11, wherein the external tactile stimuli applied includes at least one of auditory stimuli and visual stimuli.

13. The computer program product according to claim 11, wherein the external tactile stimuli applied are stimuli delivered through skin of the user.

14. The computer program product according to claim 11, wherein the external tactile stimulus is applied by an external tactile stimulus actuator configured to generate external tactile stimuli, and the external tactile stimulus actuator is positioned within a wearable device configured to be worn on a part of a foot beyond an ankle of the user.

15. The computer program product according to claim 11, wherein the tactile stimulus is applied by a stimulus applicator configured to apply a vibration to the user, inducing at least one of a response that tenses toes of the user and a response that lifts tips of the toes.

16. The computer program product according to claim 15, further comprising detecting a distance between a contact surface and the tips of the toes, wherein the stimulus applicator is configured to provide the user with the vibration that induces the response lifting the tips of the toes at least at one of a first point in time and a second point in time, the first point in time is when the distance between the contact surface and the tips of the toes is less than or equal to a first threshold value at a moment of heel landing, and the second point in time is when the distance between the contact surface and the tips of the toes is less than or equal to a second threshold value during a period from a specified time interval after toe off to heel strike.

17. The computer program product according to claim 11, wherein the tactile stimulus is applied by an auxiliary stimulus applicator configured to apply tactile stimuli of at least one of weak vibrations and strong vibrations, wherein the weak vibrations amplify tactile signals transmitted from the sole based on stochastic resonance upon ground contact, and the strong vibrations induce firing of neural impulses.

18. The computer program product according to claim 17, further comprising determining whether a gait state of the user is abnormal based on temporal changes in the center of gravity during walking, the temporal changes being calculated from the contact pressures detected by the posture information detection unit, wherein the auxiliary stimulus applicator is configured to apply tactile stimuli to the sole when a determination result of the posture determination unit indicates that the gait state is abnormal.

19. The computer program product according to claim 18, further comprising:

estimating, using a center-of-gravity change model, a part of the sole of the user where the somatosensory receptors are less functional, wherein the center-of-gravity change model is configured to output, in response to an input of the temporal changes in the center of gravity during walking of the user, an estimation result of the part of the sole where the somatosensory receptors are less functional, and the auxiliary stimulus applicator is capable of independently providing tactile stimuli to multiple parts of the sole, and is configured to apply tactile stimuli to the part where the posture determination unit has estimated that the somatosensory receptors are less functional.

20. The computer program product according to claim 11, wherein the external tactile stimuli is different than the tactile stimuli.

* * * * *